(12) United States Patent
Allegrini et al.

(10) Patent No.: US 7,375,251 B2
(45) Date of Patent: May 20, 2008

(54) PROCESSES FOR THE PREPARATION OF AMINOETHOXYBENZYL ALCOHOLS

(75) Inventors: Pietro Allegrini, San Donato Milanese (IT); Giuseppe Barreca, Montevecchia (IT); Giorgio Soriato, Caldiero (IT)

(73) Assignee: Wyeth, Madison, NJ (US)

( * ) Notice: Subject to any disclaimer, the term of this patent is extended or adjusted under 35 U.S.C. 154(b) by 29 days.

(21) Appl. No.: 11/329,503

(22) Filed: Jan. 11, 2006

(65) Prior Publication Data

US 2006/0155147 A1 Jul. 13, 2006

Related U.S. Application Data

(60) Provisional application No. 60/643,505, filed on Jan. 13, 2005.

(51) Int. Cl.
*C07C 211/00* (2006.01)
(52) U.S. Cl. .................................................. 564/338
(58) Field of Classification Search ................ 564/338
See application file for complete search history.

(56) References Cited

U.S. PATENT DOCUMENTS

| | | | |
|---|---|---|---|
| 3,914,286 A | 10/1975 | Mieville et al. | |
| 5,132,317 A * | 7/1992 | Cantello et al. | ............ 514/369 |
| 5,929,097 A | 7/1999 | Levin et al. | |
| 5,998,402 A | 12/1999 | Miller et al. | |
| 6,005,102 A | 12/1999 | Raveendranath et al. | |
| 6,242,605 B1 | 6/2001 | Raveendranath et al. | |
| 6,268,504 B1 | 7/2001 | Raveendranath et al. | |

FOREIGN PATENT DOCUMENTS

| | | |
|---|---|---|
| DE | 20 03 430 | 9/1970 |
| DE | 4438028 | 10/1994 |
| WO | WO 99/19293 * | 4/1999 |

OTHER PUBLICATIONS

Database Beilstein, Institut zur Foerderung der Chemischen Wissenschaften; Database Accession No. Reaction ID 13641, abstract.
Misra, et al., "Potential anti-tubercular compounds—Part XVI. Preparation of alpha-[p-(formyl or acetyl) aryloxy]-n-substituted acetamides and their thiosemicarbazones," *Indian J Appl Chem* (1966) 29(5-6):203-208.
Walter et al., "On certain Aromatic amines and chloracetyl derivatives," *J of the Am Chemical Society* (1919) 41:458-474.
Knorr "[Ueber die Synthese eines Piperazinderivates durch Polymerisation des Chlorathylamins und uber die Zerlegung der quateraren Salze des Piperazins durch,]" *Berichte* (1904) pp. 3507-3520.
*Remington's Pharmaceutical Sciences*, 17th ed. Mack Publishing Company, Easton PA 1985, p. 1418.
Aimoto et al. *New S-protecting Groups to Increas.e the solubility of Protectrd Lysozyme Fragments in Aqueous Buffer*, Peptide Chemistry 1978, 29-35.

* cited by examiner

*Primary Examiner*—Yvonne (Bonnie) Eyler
*Assistant Examiner*—Chukwuma O. Nwaonicha
(74) *Attorney, Agent, or Firm*—Wilmer Cutler Pickering Hale and Dorr LLP

(57) ABSTRACT

The present invention provides processes and intermediates for the preparation of aminoethoxybenzyl alcohols of Formula I useful in the production of pharmaceutically useful compounds

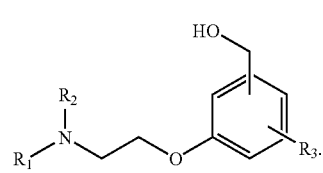

36 Claims, No Drawings

PROCESSES FOR THE PREPARATION OF AMINOETHOXYBENZYL ALCOHOLS

CROSS REFERENCE TO RELATED APPLICATIONS

The present invention claims benefit of priority from provisional U.S. Patent Application Ser. No. 60/643,505 filed Jan. 13, 2005, which is incorporated herein in its entirety.

FIELD OF THE INVENTION

This present invention relates to processes and intermediates for the preparation of aminoethoxybenzyl alcohols that can be used in the preparation of pharmaceuticals.

BACKGROUND OF THE INVENTION

Aminoethoxybenzyl alcohols are widely useful as intermediates for the preparation of various pharmaceuticals. For example, conversion of the benzylic alcohol to a halogen results in the appropriate intermediate for the preparation of indole based estrogen receptor modulators as described in, for example, U.S. Pat. No. 5,998,402. Additionally, similar benzylic halides that can be derived from their corresponding benzylic alcohols have been described as intermediates used in the preparation of compounds known to have inhibitory activity against various matrix metalloproteinase enzymes as well as against tumor necrosis factor α converting enzyme (TACE) (see, e.g., U.S. Pat. No. 5,929,097).

Previous processes for preparing aminoethoxybenzyl alcohols are reported in U.S. Pat. Nos. 6,005,102, 6,242,605 and 6,268,504, as well as PCT Pat. Appln. No. WO 99/19293. Reports of preparation of related compounds can also be found in German patent document, DE 4438028. A summary of such a method is shown in Scheme I:

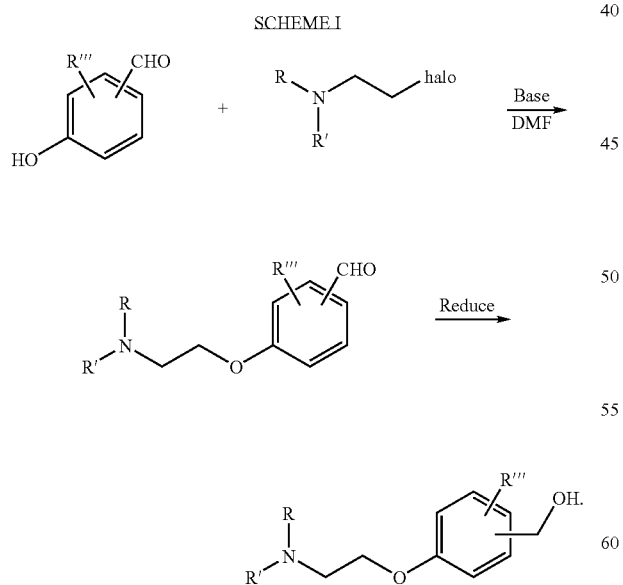

The reported synthetic methods employ unstable materials such as haloethylamines, which are well known to be difficult to handle (see, e.g., Ludwig Knorr, *Berichte*, (1904) 37: 3507). The multi-step procedures also reportedly employ dimethylformamide (DMF) as solvent, an expensive and difficult solvent to handle, especially in large scale preparations. Accordingly, more efficient methods for preparing aminoethoxybenzyl alcohols are needed. The processes and intermediates described herein help meet these and other needs.

SUMMARY OF THE INVENTION

In one aspect, the present invention provides processes for preparing a compound of Formula I:

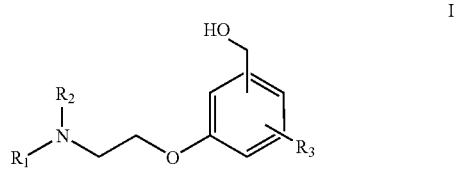

wherein:

$R_1$ and $R_2$ are, each, independently, selected from $C_1$-$C_{12}$ alkyl, heteroaryl, or aryl; or $R_1$ and $R_2$ together form $(CH_2)_n$ optionally substituted with from 1-3 substituents selected from CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl or —O-heteroaryl;

$R_3$ is H, $C_{1-6}$ alkyl, $C_{3-7}$ cycloalkyl, aryl, heteroaryl, CN, $NO_2$ or halogen;

$R_5$ and $R_{5'}$ are each, independently, H or $C_{1-6}$ alkyl; and n is 2, 3, 4, 5, 6 or 7;

comprising reducing a phenoxyacetamide of Formula VI:

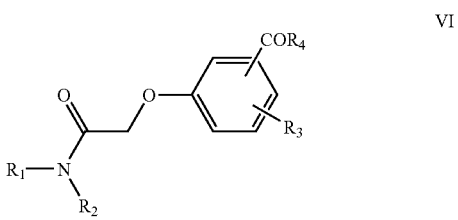

wherein $R_4$ is H or $C_{1-6}$ alkoxy; with a reducing agent for a time and under conditions effective to form the compound of Formula I.

In a further aspect, the present invention provides processes for preparing a compound of Formula I:

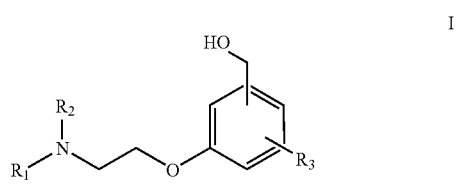

wherein the constituent variables are as define above, comprising:

a) reacting an α-haloacetamide of Formula IV:

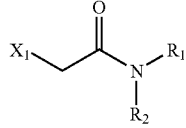

wherein $X_1$ is Cl or Br; with a compound of Formula V:

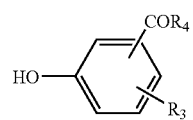

wherein $R_4$ is H or $C_{1-6}$ alkoxy; in the presence of base and optionally in the presence of a phase transfer catalyst for a time and under conditions effective to form a phenoxyacetamide of Formula VI:

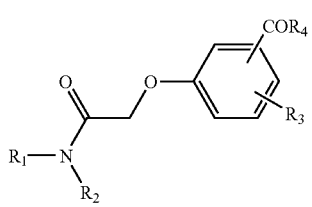

and b) reducing the phenoxyacetamide of Formula VI with a reducing agent for a time and under conditions effective to form the compound of Formula I.

In a further aspect, the present invention provides a process for preparing a compound of Formula I:

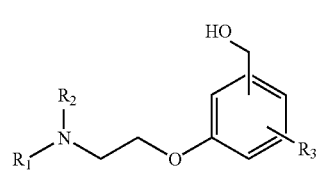

wherein the constituent variables are as defined above; comprising:

a) reacting an acid halide of Formula II:

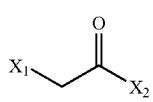

wherein $X_1$ and $X_2$ are each, independently, Cl or Br with an amine of Formula III:

for a time and under conditions effective to form an α-haloacetamide of Formula IV:

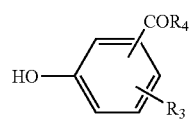

b) reacting the α-haloacetamide of Formula IV with a compound of Formula V:

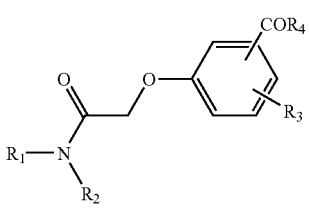

wherein $R_4$ is H or $C_{1-6}$ alkoxy; in the presence of base and optionally in the presence of a phase transfer catalyst for a time and under conditions effective to form a phenoxyacetamide of Formula VI:

and c) reducing the phenoxyacetamide of Formula VI with a reducing agent for a time and under conditions suitable for forming the compound Formula I.

In some embodiments, the base comprises an inorganic carbonate such as $Na_2CO_3$ or $K_2CO_3$.

In some embodiments, the reducing agent comprises lithium aluminum hydride or sodium bis(2-methoxyethoxy)-aluminum hydride, preferably, sodium bis(2-methoxyethoxy)-aluminum hydride.

In some embodiments, one or more steps of the processes of the invention are carried out in the presence of solvent. In some embodiments, the solvent comprises an aromatic hydrocarbon solvent, a halogenated hydrocarbon solvent or an ether solvent. In some embodiments, the solvent comprises an aromatic hydrocarbon solvent, preferably, toluene.

In some embodiments, a phase transfer catalyst is present in the reaction of compounds IV and V. In some embodiments, the phase transfer catalyst is a quaternary amine, for example, tricaprylmethylammonium chloride In some embodiments, the invention provides compounds prepared by the processes described herein.

The present invention further provides compounds of Formula VI:

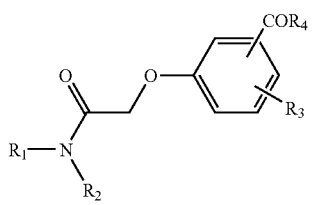

wherein:

$R_1$ and $R_2$ are, each, independently, selected from $C_1$-$C_{12}$ alkyl, heteroaryl or aryl; or $R_1$ and $R_2$ together form $(CH_2)_n$ optionally substituted with from 1-3 substituents selected from CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl or —O-heteroaryl;

$R_3$ is H, $C_{1-6}$ alkyl, $C_{3-7}$ cycloalkyl, aryl, heteroaryl, CN, $NO_2$ or halogen;

$R_4$ is H or $C_1$ alkoxy;

$R_5$ and $R_{5'}$ are each, independently, H or $C_{1-6}$ alkyl; and n is 2, 3, 4, 5, 6 or 7.

In some embodiments of the present compounds and processes, $R_1$ and $R_2$ together form a group of formula —$(CH_2)_n$— that is optionally substituted with from 1-3 substituents selected from CN, $NO_2$, $C_{1-6}$ alkyl, $C_{3-7}$ cycloalky, aryl, heteroaryl, halogen, OH, $NR_5R_{5'}$, CHO, $COOR_5$, $CONR_5R_{5'}$, $SR_5$, —O-aryl or —O-heteroaryl.

In some embodiments of the present compounds and processes, $R_1$ and $R_2$ together form —$(CH_2)_4$—, —$(CH_2)_5$— or —$(CH_2)_6$—, preferably, —$(CH_2)_6$—.

In some embodiments of the present compounds and processes, $R_3$ is H, $C_{1-6}$ alkyl or halogen, preferably, H.

In further embodiments of the present compounds and processes, $R_1$ and $R_2$ together form —$(CH_2)_n$— optionally substituted with from 1-3 substituents selected from CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl or —O-heteroaryl; $R_3$ is H, $C_{1-6}$ alkyl or halogen; and n is 4, 5 or 6. Preferably, $R_3$ is H and n is 6. More preferably, $R_1$ and $R_2$ together form —$(CH_2)_6$— and $R_3$ is H.

In some embodiments of the present compounds and processes, $X_1$ is Cl, or $X_2$ is Cl, or both $X_1$ and $X_2$ are Cl.

In some further embodiments of the present compounds and processes, $R_4$ is H.

In some embodiments of the present compounds and processes, the group of formula $COR_4$ is in the para position relative to the phenolic hydroxyl group of formula V. In further embodiments of the present compounds and processes, the group of formula $COR_4$ is in the para position relative to the $OCH_2CONR_1R_2$ group of formula VI. In some such embodiments of the present compounds and processes, $X_1$ is Cl, or $X_2$ is Cl, or both $X_1$ and $X_2$ are Cl.

DETAILED DESCRIPTION OF EMBODIMENTS OF THE INVENTION

The present invention is directed to, inter alia, processes for the preparation of compounds of Formula I that can be employed in the preparation of, for example, inhibitors of matrix metalloproteinases and tumor necrosis factor α converting enzyme (TACE) inhibitors, which are useful in the treatment of various diseases including arthritis, tumor metastasis, tissue ulceration, abnormal wound healing, periodontal disease, bone disease, proteinuria, aneurysmal aortic disease, degenerative cartilage loss following traumatic joint injury, demyelinating dieseases of the nervous system, HIV infection, osteoporosis, prostatic hypertorphy, infertility, breast cancer, endometrial hyperplasia and cancer, cardiovascular disease, contraception, Alzheimer's disease, and melanoma (see, e.g., WO 99/19293).

In some embodiments, the present invention provides a process for preparing a compound of Formula I:

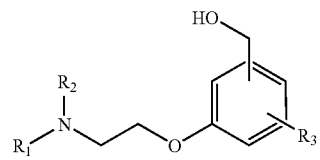

wherein:

$R_1$ and $R_2$ are each, independently, selected from the group consisting of $C_1$-$C_{12}$ alkyl, heteroaryl and aryl; or $R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl and —O-heteroaryl;

$R_3$ is selected from the group consisting of H, $C_{1-6}$ alkyl, $C_{3-7}$ cycloalkyl, aryl, heteroaryl, CN, $NO_2$ and halogen;

$R_5$ and $R_{5'}$ are each, independently, H or $C_{1-6}$ alkyl; and n is 2, 3, 4, 5, 6 or 7;

comprising reacting a phenoxyacetamide of Formula VI:

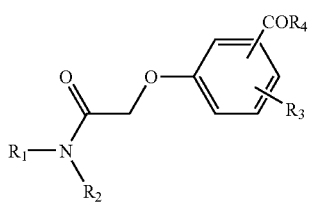

wherein $R_4$ is H or $C_{1-6}$ alkoxy; with a reducing agent for a time and under conditions effective to form said compound of Formula I;

wherein optionally the phenoxyacetamide of Formula VI is formed by a process comprising:

a) reacting an α-haloacetamide of Formula IV:

IV wherein $X_1$ is Cl or Br; and wherein optionally the α-haloacetamide of Formula IV is formed by a process comprising:

i) reacting an acid halide of Formula II:

II wherein $X_1$ and $X_2$ are each, independently, Cl or Br; with an amine of Formula III:

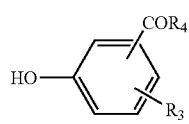

III for a time and under conditions effective to form an α-haloacetamide of Formula IV:

b) with a compound of Formula V:

V wherein $R_4$ is H or $C_{1-6}$ alkoxy;

in the presence of base and optionally in the presence of a phase transfer catalyst for a time and under conditions effective to form the phenoxyacetamide of Formula VI.

A general outline of the processes of the present invention is provided in Scheme II, where constituent members of the depicted compounds of Formulas I, II, III, IV, V, and VI are defined hereinbelow.

SCHEME II

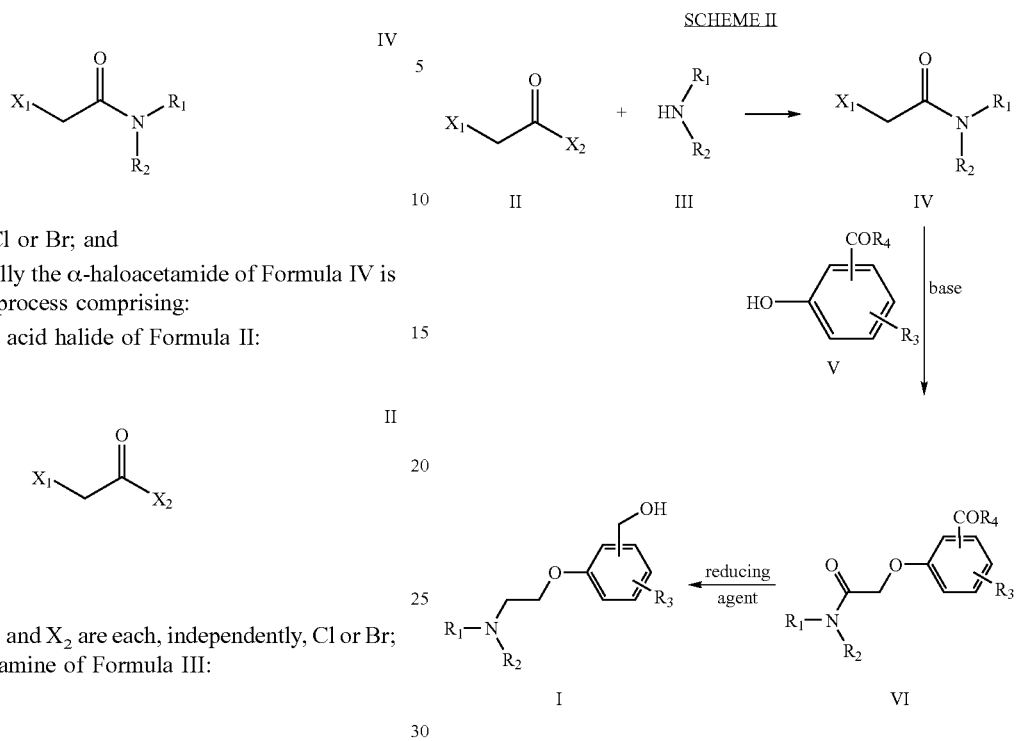

Constituent members of compounds of Formulas I, II, III, IV, V, and VI according to the compounds and processes provided herein are as described supra.

According to some embodiments, $R_1$ and $R_2$ together form $(CH_2)_n$ optionally substituted with from 1-3 substituents selected from CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O— aryl or —O-heteroaryl; $R_3$ is H, $C_{1-6}$ alkyl or halogen; and n is 4, 5 or 6.

According to further embodiments, $R_1$ and $R_2$ together form $(CH_2)_n$ optionally substituted with from 1-3 substituents selected from CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O— aryl or —O-heteroaryl; $R_3$ is H; and n is 6.

In some further embodiments, $R_1$ and $R_2$ together form $(CH_2)_6$ and $R_3$ is H.

The present invention provides, in part, a process for preparing a compound Formula I:

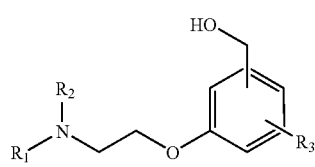

I comprising reacting a phenoxyacetamide of Formula VI:

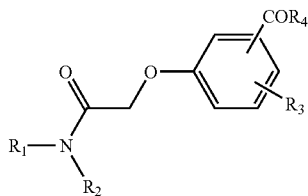

with a reducing agent for a time and under conditions suitable for forming the compound Formula I.

Suitable reducing agents include inorganic metal hydrides such as aluminum hydride salts. Some examples of aluminum hydride salts include lithium aluminum hydride (LAH), sodium bis(2-methoxyethoxy)-aluminum hydride (commercially available as VITRIDE®), and the like. Suitable reducing agents can, for example, concomitantly reduce the amide and $COR_4$ moieties to their respective amine and alcohol. The reducing agent can be provided in molar excess (more reducing equivalents than theoretically needed to reduce the full amount of compound of Formula VI to the compound of Formula I), and/or combined with the compound of Formula VI in such a way that the reducing agent is present in molar excess for the duration of the addition (e.g., compound of Formula VI in solution can be added to a vessel containing at least enough reducing agent to fully reduce the compound of Formula VI to a compound of Formula I).

The reduction can be conducted at any reasonable temperature that does not lead to any substantial decomposition of reactants, products or solvent (if present). The temperature at which the reduction is carried out can be controlled by well known techniques. For example, the reaction temperature can be maintained between about 15 to about 35° C., about 20 to about 30° C. or about 20 to about 25° C.

Compounds of Formula VI can be prepared by any method such as an alkylation reaction involving the reacting of an α-haloacetamide of Formula IV:

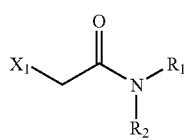

with a compound of Formula V:

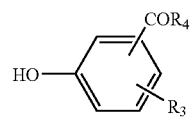

in the presence of base and optionally in the presence of a phase transfer catalyst for a time and under conditions suitable for forming the phenoxyacetamide of Formula VI.

Suitable bases for the alkylation reaction can contain inorganic carbonates such as alkaline earth carbonates and alkali carbonates, inorganic hydroxides such as alkaline earth hydroxides and alkali hydroxides, and inorganic hydrides such as alkali hydrides, and the like. According to some embodiments, the base is an alkali carbonate such as $K_2CO_3$ or $Na_2CO_3$. Base can be present in the reaction in molar excess with respect to the compound of Formula V. In some embodiments, the a molar ratio (base:compound of Formula V) can be about 1.01 to about 1.5, about 1.01 to about 1.3 or about 1.01 to about 1.2.

Suitable phase transfer catalysts include quaternary amine salts such as tetralkylammonium halides (e.g., tetrabutylammonium bromide, tricaprylmethylammonium chloride (ALIQUAT®), etc.) and aralkyltrialkylammonium halides (e.g., benzyltrimethylammonium chloride). Other suitable phase transfer catalysts include phosphonium salts and crown ethers. The phase transfer catalyst can be provided in a catalytic amount (e.g., amount sufficient to accelerate the alkylation reaction rate), such as in a molar ratio (phase transfer catalyst:compound of Formula V) of about 0.01, about 0.05, about 0.1, about 0.2, about 0.5 or less than about 1.0.

The alkylation can be carried out at elevated temperature, such as reflux temperature. In some embodiments, elevated temperature is about 30 to about 150° C., 50 to about 120° C., or about 80 to about 120° C. or about 110 to about 115° C. The reaction can be maintained at elevated temperature for enough time to ensure substantial reaction completion, such as for example, about 1 to about 24 hours, about 2 to about 12 hours or about 2 to about 5 hours.

In some preferred embodiments, the compound of Formula V is a 4-hydroxybenzoate alkyl ester or 4-hydroxybenzaldehyde, preferably, 4-hydroxybenzaldehyde.

Compounds of Formula IV can be prepared by any method such as a reaction involving the reaction of an acid halide of Formula II:

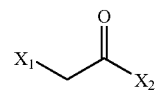

with an amine of Formula III:

for a time and under conditions suitable for forming the α-haloacetamide of Formula IV.

The reaction can be carried out such that the amine of Formula III is provided in molar excess relative to the amount of compound of Formula II. For example, the molar ratio (compound of Formula III: compound of Formula II) can be about 1.1, about 1.5, about 2.0, about 2.5, about 3, about 5 or about 10. The condensation reaction can be carried out at any suitable temperature such as from about −10 to about 25° C., about −10 to about 10° C. or about −5 to about 5° C.

The reaction can further be conducted in the presence of a tertiary amine such as a trialkyamine (e.g., trimethylamine, triethylamine, etc). The tertiary amine can be present in a catalytic amount.

In some embodiments, the compound of Formula II is α-chloroacetyl chloride. In some further embodiments, the compound of Formula III is pyrrolidine, piperidine or hexamethyleneimine, preferably, hexamethyleneimine.

In some embodiments of the invention, multi-step processes are carried out stepwise and each intermediate is isolated before proceeding to the next step. In other embodiments of the invention, some of the intermediates are isolated and others are not. In yet other embodiments, none of the intermediates are completely isolated and all of the reactions take place in a single reactor vessel.

The processes described herein have numerous advantages readily apparent to the skilled artisan. For example, the use of unstable haloethylamines is avoided, and less costly solvents can be used than for similar processes. Furthermore, the entire reaction sequence can be typically accomplished in a one-pot procedure leading to a more efficient preparation.

The processes of the invention can be performed on any desired scale, for example, milligram scale or gram scale. In some embodiments, the processes are performed on the larger scales, i.e., kilogram scale or larger.

It is understood in the generic description above and for other groups described herein that, in each instance, any variable group may be independently substituted by their allowed groups. Thus, for example, where a structure is described wherein two $R_2$ groups are simultaneously present on the same compound, the two $R_2$ groups can represent different groups.

The term "alkyl", employed alone, is defined herein as, unless otherwise stated, either a straight-chain or branched saturated hydrocarbon moiety. In some embodiments, the alkyl moiety contains 1 to 12, 1 to 10, 1 to 8, 1 to 6, or 1 to 4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl, higher homologs such as n-pentyl, n-hexyl, n-heptyl, n-octyl, and the like.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-8 or 3-7 carbon atoms. Any suitable ring position of the cycloalkyl moiety can be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, and the like.

The terms "halo" or "halogen", employed alone or in combination with other terms, is defined herein as, unless otherwise stated, fluoro, chloro, bromo or iodo.

The term "aryl", employed alone or in combination with other terms, is defined herein as, unless otherwise stated, an aromatic carbocyclic moiety of up to 14 carbon atoms, e.g., 6-14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. Aryl moieties can be optionally substituted by one or more substituents selected from halo, $C_1$-$C_4$ alkyl, $C_1$-$C_4$ alkoxy, CN or $NO_2$.

The term "arylalkyl" or "aralkyl," employed alone or in combination with other terms, is defined herein as, unless otherwise stated, an alkyl, as herein before defined, suitably substituted on any open ring position with an aryl moiety wherein the alkyl chain is a saturated hydrocarbon moiety. In some embodiments, the alkyl moiety has from 1 to 8, 1 to 6, or 1 to 4 carbon atoms. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

As used herein, "heteroaryl" groups are aromatic heterocarbocyclyl groups and include monocyclic and polycyclic aromatic hydrocarbons that have at least one heteroatom ring member (e.g., 1 to 4) such as sulfur, oxygen, or nitrogen and 5-20 ring members. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzothiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms. Heteroaryl groups can be optionally substituted by one or more substituents selected from halo, $C_1$-$C_4$ alkyl, $C_1$-$C_4$ alkoxy, CN or $NO_2$ group.

The term "alkoxy", employed alone or in combination with other terms, is defined herein as, unless otherwise stated, —O-alkyl. Examples of alkoxy moieties include, but are not limited to, chemical groups such as methoxy, ethoxy, isopropoxy, sec-butoxy, tert-butoxy, and homologs, isomers, and the like.

The compounds of the present invention can contain an asymmetric atom, and some of the compounds can contain one or more asymmetric atoms or centers, which can thus give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography and high-performance liquid chromatography.

The compounds provided herein can also include their salts formed from, for example, mineral or organic acid salts of basic residues such as amines, alkali or organic salts of acidic residues such as carboxylic acids, and the like. The invention includes acceptable salt forms formed from the addition reaction with either inorganic or organic acids. Additionally, this invention includes quaternary ammonium salts of the compounds herein, which can be prepared by reacting the nucleophilic amines with a suitably reactive alkylating agent such as an alkyl halide or benzyl halide. Lists of suitable salts are found in *Remington's Pharmaceu-* tical Sciences, 17th ed., Mack Publishing Company, Easton, Pa., 1985, p. 1418, the disclosure of which is hereby incorporated by reference.

As used herein, the term "reacting" refers to the bringing together of designated chemical reactants such that a chemical transformation takes place generating a compound different from any initially introduced into the system. Reacting can take place in the presence or absence of solvent.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible) or mass spectrometry, or by chromatography such as high performance liquid chromatograpy (HPLC) or thin layer chromatography.

The reactions of the processes described herein can be carried out in suitable solvents that can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas. Some example solvents suitable for the processes described herein include halogenated hydrocarbons (e.g., methylene chloride), aromatic hydrocarbons (e.g., benzene, toluene, etc.), and ethers (e.g., diethyl ether, tetrahydrofuran). In some embodiments, the solvent is an aromatic hydrocarbon such as toluene.

The reactions of the processes described herein can be carried out at appropriate temperatures that can be readily determined by the skilled artisan. Reaction temperatures will depend on, for example, the melting and boiling points of the reagents and solvent, if present, the thermodynamics of the reaction (e.g., vigorously exothermic reactions are typically carried out at reduced temperatures) and the kinetics of the reaction (e.g., a high activation energy barrier typically necessitates elevated temperatures). "Elevated temperature" refers to temperatures above room temperature (about 20° C.) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

EXAMPLE

PREPARATION OF [4-(2-HEXAMETHYLENE-IMINO-1-YL-ETHOXY)-PHENYL]-METHANOL

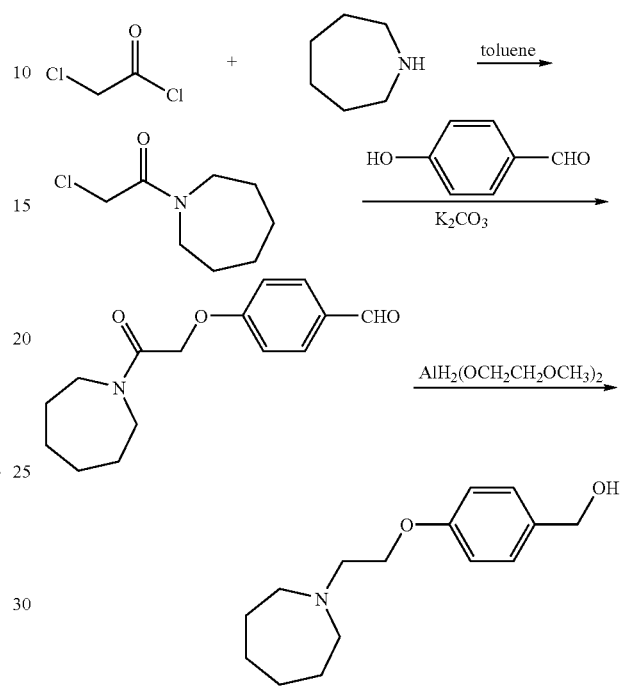

Preparation of
1-Hexamethyleneimin-1-Yl-2-Chloro-Ethanone

Hexamethyleneimine (76.4 kg) was added to a solution of 2-chloro-acetyl chloride (43.5 kg) and toluene (200 kg) maintaining the temperature between 0° C. and −3° C. At the end of the reaction, water (57.8 kg) was slowly added and the resultant mixture was heated to 20-25° C. The aqueous layer was discharged and the organic layer containing 1-chloroacetyl-hexamethyleneimine was used in the subsequent step without any further purification.

Preparation of
4-(2-Oxo-2-Hexamethyleneimino-Ethoxy)-Benzaldehyde

The phase transfer catalyst tricaprylmethylammonium chloride, $K_2CO_3$ (58.5 Kg), 4-hydroxybenzaldehyde (50 kg) and toluene (8.5 kg to rinse the lines) were added to the solution of 1-chloroacetyl-hexamethyleneimine obtained from the previous step. The resulting mixture was heated to reflux temperature and water was removed by azeotropic distillation. In this way, the suspension reached the internal temperature of 112° C.-113° C. At the end of the reaction, the mixture was cooled at 65° C. Water (115.5 kg) was added to the reaction and the resultant mixture was kept under stirring for 30 minutes. The aqueous layer was separated and the organic solution was washed with at 55-65° C. with diluted sodium hydroxide (72.6 kg of NaOH 4% w/w) and then with water (57.6 kg). Water was removed by azeotropic distillation and the resultant solution was concentrated by vacuum distillation until a residual volume of 240 liters was reached. The resultant solution was kept at 60° C. to prevent spontaneous crystallization of 4-(2-oxo-2-hexamehtylene-imino-ethoxy)-benzaldehyde.

Preparation of 4-(2-Hexamethyleneimino-Ethoxy)-Benzyl Alcohol

The solution from the previous step was added to sodium bis(2-methoxyethoxy)-aluminum hydride (179.9 kg) diluted with toluene (38.7 kg). During the addition, the temperature was kept between 20° C. and 30° C. At the end of the reaction, the mixture was poured into 15% w/w sodium hydroxide (176.2 kg). During the quenching, the temperature was kept below 30° C. Toluene was then charged (56.8 kg) and the aqueous layer was separated. After several washings with water (overall amount 265 kg divided into 5 portions), the organic phase was submitted to azeotropic distillation of the residual moisture. The resultant toluene solution was cooled at 20-25° C. According to the HPLC assay of the mixture, 84.5 kg of 4-(2-hexamethyleneimino-ethoxy)-benzyl alcohol was obtained (88% from 2-chloro-acetyl chloride).

It is intended that each of the patents, applications, and printed publications, including books, mentioned in this patent document be hereby incorporated by reference in their entirety.

As those skilled in the art will appreciate, numerous changes and modifications may be made to the embodiments of the invention without departing from the spirit of the invention. It is intended that all such variations fall within the scope of the invention.

What is claimed is:

1. A process for preparing a compound of Formula I:

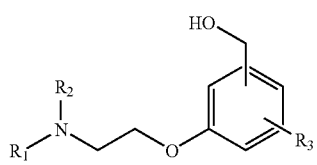

wherein:
- $R_1$ and $R_2$ are each, independently, selected from the group consisting of $C_1$-$C_{12}$ alkyl, heteroaryl and aryl; or
- $R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl and —O-heteroaryl;
- $R_3$ is selected from the group consisting of H, $C_{1-6}$ alkyl, $C_{3-7}$ cycloalkyl, aryl, heteroaryl, CN, $NO_2$ and halogen;
- $R_5$ and $R_{5'}$ are each, independently, H or $C_{1-6}$ alkyl; and
- n is 2, 3, 4, 5, 6 or 7;

comprising:
a) reacting an α-haloacetamide of Formula IV:

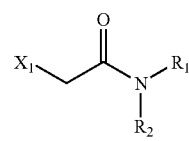

wherein $X_1$ is Cl or Br, and $R_1$ and $R_2$ are defined as hereinabove;
with a compound of Formula V:

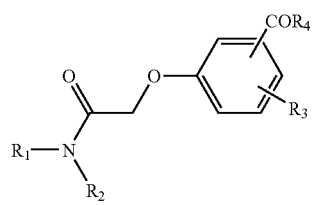

wherein $R_4$ is H or $C_{1-6}$ alkoxy, and $R_3$ is defined as hereinabove;
in the presence of base and optionally in the presence of a phase transfer catalyst for a time and under conditions effective to form a phenoxyacetamide of Formula VI

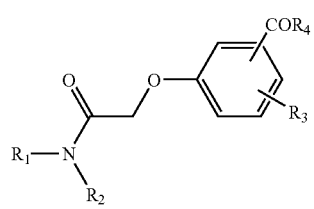

wherein $R_1$, $R_2$, $R_3$, and $R_4$, are defined as hereinabove;
b) reacting the phenoxyacetamide of Formula VI with a reducing agent for a time and under conditions effective to form said compound of Formula I.

2. The process of claim 1 wherein $R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl and —O-heteroaryl.

3. The process of claim 2 wherein $R_1$ and $R_2$ together form —$(CH_2)_4$—, —$(CH_2)_5$— or —$(CH_2)_6$—.

4. The process of claim 2 wherein $R_1$ and $R_2$ together form —$(CH_2)_6$—.

5. The process of claim 1 wherein $R_3$ is H, $C_{1-6}$ alkyl or halogen.

6. The process of claim 5 wherein $R_3$ is H.

7. The process of claim 1 wherein $R_4$ is H.

8. The process of claim 1 wherein the $COR_4$ group in formula VI is in the para position relative to $OCH_2CONR_1R_2$.

9. The process of claim 1 wherein:
- $R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl and —O-heteroaryl;

$R_3$ is H, $C_{1-6}$ alkyl or halogen;

$R_4$ is H; and n is 4, 5 or 6.

10. The process of claim 1 wherein:

$R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_5'$, $SR_5$, —O-aryl and —O-heteroaryl;

$R_3$ is H;

$R_4$ is H; and n is 6.

11. The process of claim 1 wherein:

$R_1$ and $R_2$ together form —$(CH_2)_6$—;

$R_3$ is H; and $R_4$ is H.

12. The process of claim 1 wherein the reducing agent comprises lithium aluminum hydride or sodium bis(2-methoxyethoxy)-aluminum hydride.

13. The process of claim 12 wherein the reducing agent is sodium bis(2-methoxyethoxy)-aluminum hydride.

14. The process of claim 1 wherein the reacting steps are carried out in the presence of solvent.

15. The process of claim 14 wherein the solvent comprises an aromatic hydrocarbon solvent, a halogenated hydrocarbon solvent or an ether solvent.

16. The process of claim 14 wherein the solvent comprises an aromatic hydrocarbon solvent.

17. The process of claim 14 wherein the solvent comprises toluene.

18. The process of claim 1 wherein $X_1$ is Cl.

19. The process of claim 1 wherein the base comprises an inorganic carbonate.

20. The process of claim 19 wherein the inorganic carbonate is $Na_2CO_3$ or $K_2CO_3$.

21. The process of claim 1 wherein the phase transfer catalyst is present.

22. The process of claim 21 wherein the phase transfer catalyst is tricaprylmethylammonium chloride.

23. The process of claim 1 wherein $X_2$ is Cl.

24. The process of claim 1 wherein $X_1$ and $X_2$ are both Cl.

25. A process for preparing a compound of Formula I:

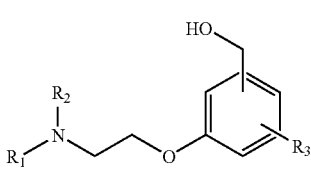

wherein:

$R_1$ and $R_2$ are each, independently, selected from the group consisting of $C_1$-$C_{12}$ alkyl, heteroaryl and aryl; or $R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_5$, $SR_5$ —O-aryl and —O-heteroaryl;

$R_3$ is selected from the group consisting of H, $C_{1-6}$ alkyl, $C_{3-7}$ cycloalkyl, aryl, heteroaryl, CN, $NO_2$ and halogen;

$R_5$ and $R_{5'}$ are each, independently, H or $C_{1-6}$ alkyl; and n is 2, 3, 4, 5, 6 or 7;

comprising:

a) reacting an acid halide of Formula II:

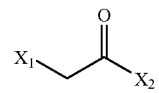

wherein $X_1$ and $X_2$ are each, independently, Cl or Br;

with an amine of Formula III:

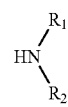

wherein $R_1$ and $R_2$ are defined as hereinabove;

for a time and under conditions effective to form an α-haloacetamide of Formula IV:

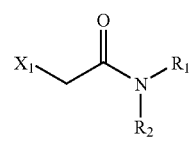

wherein $X_1$, $R_1$ and $R_2$ are defined as hereinabove;

b) reacting the α-haloacetamide of Formula IV with a compound of Formula V:

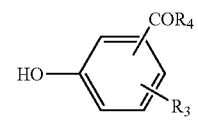

wherein $R_4$ is H or $C_{1-6}$ alkoxy;

in the presence of base and optionally in the presence of a phase transfer catalyst for a time and under conditions effective to form a phenoxyacetamide of Formula VI

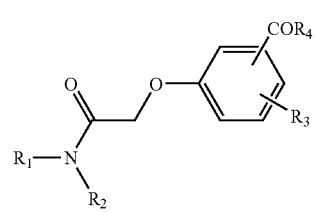

wherein $R_1$, $R_2$, $R_3$ and $R_4$ are defined as hereinabove; and c) reacting the phenoxyacetamide of Formula VI with a reducing agent for a time and under conditions effective to form said compound of Formula I.

26. The process of claim 25 wherein:

$R_1$ and $R_2$ together form a group of formula —$(CH_2)_n$— that is optionally substituted with from 1-3 substituents selected from the group consisting of CN, $NO_2$, $C_{1-6}$ alkyl, $C_{3-7}$ cycloalkyl, aryl, heteroaryl, halogen, OH, $NR_5R_{5'}$, CHO, $COOR_5$, $CONR_5R_{5'}$, $SR_5$, —O-aryl and —O-heteroaryl;

$R_3$ is H, $C_{1-6}$ alkyl or halogen;

$R_4$ is H; and n is 4, 5 or 6.

27. The process of claim 25 wherein:

$R_1$ and $R_2$ together form —$(CH_2)_6$—;

$R_3$ is H;

$R_4$ is H.

28. The process of claim 25 wherein the reducing agent comprises lithium aluminum hydride or sodium bis(2-methoxyethoxy)-aluminum hydride.

29. The process of claim 25 wherein the reducing agent is sodium bis(2-methoxyethoxy)-aluminum hydride.

30. The process of claim 25 wherein $X_1$ is Cl.

31. The process of claim 25 wherein the base comprises an inorganic carbonate.

32. The process of claim 31 wherein the inorganic carbonate is $Na_2CO_3$ or $K_2CO_3$.

33. The process of claim 25 wherein the phase transfer catalyst is present.

34. The process of claim 33 wherein the phase transfer catalyst is tricaprylmethylammonium chloride.

35. The process of claim 25 wherein $X_2$ is Cl.

36. The process of claim 25 wherein $X_1$ and $X_2$ are both Cl.

* * * * *